(12) United States Patent
Watanabe et al.

(10) Patent No.: US 6,190,613 B1
(45) Date of Patent: Feb. 20, 2001

(54) SAMPLE CONCENTRATION DEVICE

(75) Inventors: Chuichi Watanabe; Akihiko Hosaka; Kunitaka Sato; Masami Morikawa, all of Fukushima; Shin Tsuge, Aichi, all of (JP)

(73) Assignee: Frontier Laboratories Ltd., Fukushima (JP)

( * ) Notice: Under 35 U.S.C. 154(b), the term of this patent shall be extended for 0 days.

(21) Appl. No.: 09/302,251

(22) Filed: Apr. 30, 1999

(30) Foreign Application Priority Data

| Apr. 30, 1998 | (JP) | 10/121171 |
| Jul. 23, 1998 | (JP) | 10/208161 |
| Oct. 1, 1998 | (JP) | 10/279828 |
| Mar. 5, 1999 | (JP) | 11/058605 |

(51) Int. Cl.$^7$ ................................................ G01N 30/02
(52) U.S. Cl. ............................. 422/99; 422/89; 422/101; 73/23.41; 95/87; 95/89; 96/103; 96/104; 96/105
(58) Field of Search ................................ 22/99, 89, 101; 95/87, 89; 96/103, 104, 105; 73/23.41

(56) References Cited

U.S. PATENT DOCUMENTS 4,422,860 * 12/1983 Feinstein .

FOREIGN PATENT DOCUMENTS 60-20144 * 2/1985 (JP) .
6-308110 * 11/1994 (JP) .
11-295292 * 10/1999 (JP) .

* cited by examiner

Primary Examiner—Jan Ludlow
(74) Attorney, Agent, or Firm—Paul A. Guss

(57) ABSTRACT

A sample concentration device is provided in which a gaseous sample is concentrated by cooling a portion of a gas transfer line through which the sample is introduced into a detecting apparatus, such as a gas chromatograph or the like. The device is characterized by a cooling device for cooling a portion of the gas transfer line, which is housed in a constant temperature chamber, by spraying a coolant from a nozzle facing the portion of the gas transfer line, and by a gas flow device for creating a substantially dry gas flow through the nozzle to prevent the nozzle from becoming plugged with ice formed by freezing of moisture in the air inside the constant temperature chamber when the coolant spray is stopped. An outer jacket surrounding a portion of the gas transfer line which is subjected to cooling is also disclosed. Because the gas transfer line is locally cooled by spraying the coolant from the nozzle, the sample introduced from the sample injection port is condensed at the cooled portion, and further owing to the presence of the outer jacket, as a result, each component of the sample is shown by a single peak, as opposed to multiple peaks per component, when the components are detected by the detecting apparatus.

11 Claims, 6 Drawing Sheets

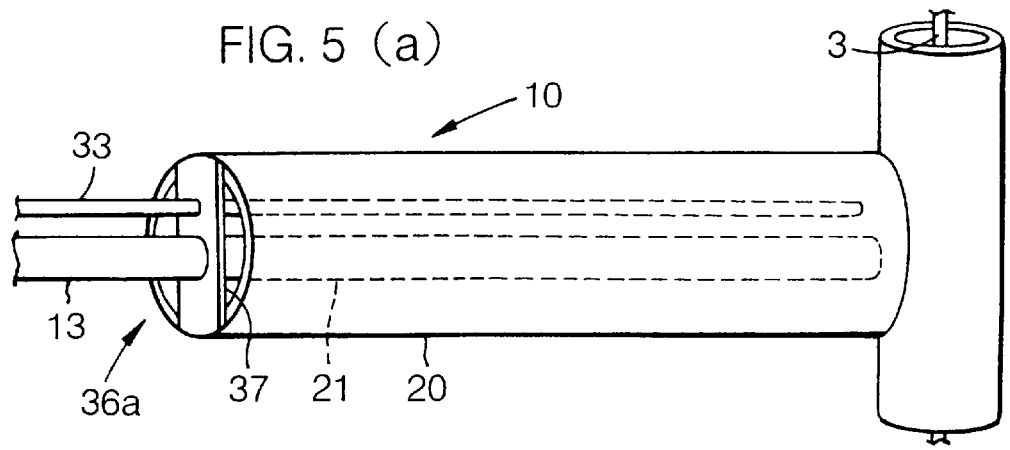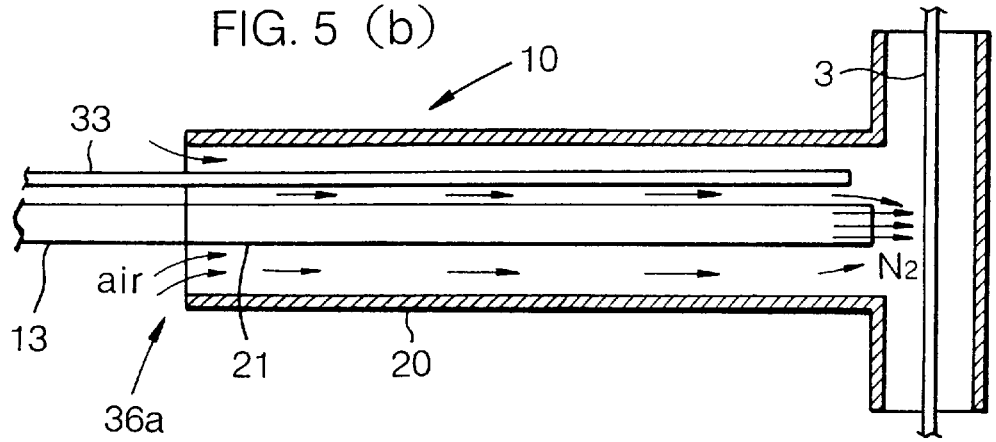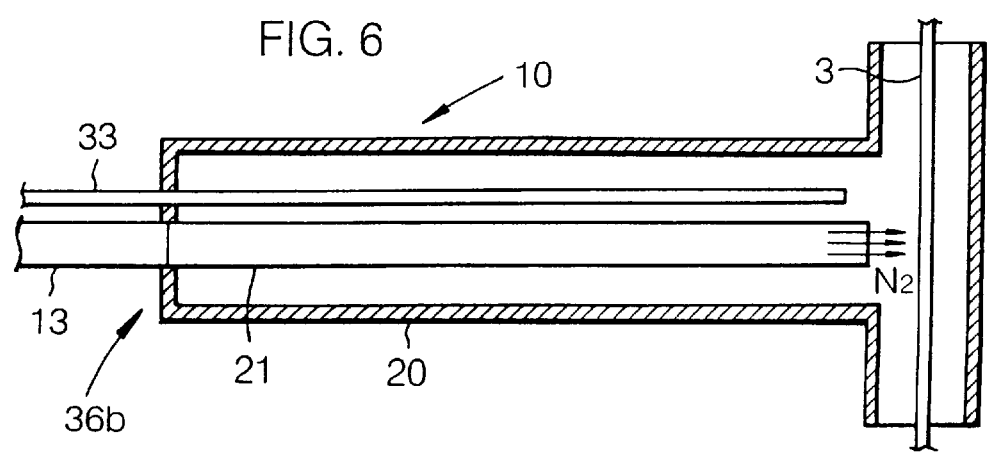

SAMPLE CONCENTRATION DEVICE

BACKGROUND OF THE INVENTION

This invention relates to a gaseous sample concentration device that, upon analyzing a gaseous or liquid sample composed of multiple components using an apparatus such as a gas chromatograph, concentrates the gaseous sample at a certain position in the gas transfer line that transfers the gas into the apparatus.

Description of the Related Art

Apparatus, such as gas chromatographs, are available for analyzing gaseous or liquid samples composed of multiple components by introduction of such gas or liquid samples into a detector via a gas transfer line.

The gas chromatograph unit analyzes a gaseous sample composed of multiple components, first by injecting the sample using a micro-syringe or the like into a sample injection port located at one end of a separation column such as a capillary column or the like housed in a constant temperature chamber, then by separating the sample into each component in the separation column, and by detecting each separated component using a detector located at the other end of the separation column. The detector that is typically employed is a mass spectrometer or hydrogen flame ionization detector. Using the gas chromatograph, a gas chromatogram showing peaks to indicate the detection intensity (concentration) of each component along with corresponding retention times can be obtained as a result of this analysis.

For improving accuracy of the analysis, it is desirable when using the gas chromatograph that a single component be detected by a single isolated peak, and not be broken into multiple peaks. For this, it is required that the gaseous sample be introduced at the narrowest volume possible at the end of the separation column. In order for the gaseous sample injected into the separation column in the gas chromatograph to be concentrated within the narrowest possible volume, a conceivable method is to inject a required amount of the sample with a micro-syringe or the like. However, in the case that the concentration of the sample is very low, a large amount of sample, for example a few ml, needs to be injected. This is time-consuming and, therefore, is not at all a practical process to be implemented. Another conceivable method is to cool the entire column to a temperature below the ambient temperature so that the sample injected in the column becomes condensed and concentrated. This method, on the other hand, requires a large amount of refrigerant. Also, as the minimum attainable temperature is only −80° C., trapping of low boiling-point compounds, such a hydrocarbons with carbon numbers less than 10, is almost impossible.

There is a conventionally known method wherein a portion of one side of the separation column to which the sample is introduced is wound in a coil and is cooled by dipping it into liquid nitrogen placed in a Dewar vessel. In this method, after the gas sample is condensed within that portion, the separation column is taken out of the Dewar vessel and is placed in a constant temperature chamber. By these processes, the temperature inside of the separation column is raised and the condensed sample desorbs thermally, and the components of the sample are further separated from each other by the separation column.

This method can almost perfectly condense and trap a sample consisting of multiple components having carbon numbers of greater than 3 or 4 (i.e., propane or butane in the case of hydrocarbon) at the cooled portion. As a result, each component that is trapped thereby is detected by a single peak.

The above-described method can be practiced in the laboratory. However, implementing it is still cumbersome due to the fact that all the steps usually have to be carried out manually, since it has proven difficult to automate the method.

In order to solve the aforementioned problem, a method can be considered in which a nozzle for spraying liquid nitrogen is placed facing a portion of the separation column in the neighborhood of the sample injection port, whereby the portion of the separation column is directly cooled with liquid nitrogen that is sprayed from the nozzle. By this method, the portion of the separation column can be locally cooled to the temperature of liquid nitrogen (−196° C.) within a constant temperature chamber which is otherwise kept at a desired temperature, 40° C. for example. It is therefore expected that the sample injected into the sample injection port can be condensed at the cooled portion of the column and that each component can be detected as a corresponding single peak.

However, upon cooling by liquid nitrogen using this method, moisture in the air condenses and freezes around the cooled portion of the separation column, and after the nitrogen spray stops, the air inside the constant temperature chamber enters into the nozzle and moisture existing in the air freezes into ice inside of the nozzle. This will create a problem in that the open end of the nozzle becomes plugged up with ice, making subsequent sprays of the liquid nitrogen difficult.

SUMMARY OF THE INVENTION

The present invention provides a device which concentrates a gaseous sample without causing plugging of the nozzle with ice when the gaseous sample is concentrated by cooling with a coolant spray at a portion of the gas transfer line in which the sample is introduced.

The sample concentration device of the present invention concentrates a sample in the vicinity of the sample injection port, wherein a sample consisting of multiple components can then be analyzed by introducing the sample via the sample injection port, and by transferring the sample to a detector through the gas transfer line which is housed in a constant temperature chamber. The device is characterized by a cooling means for cooling a portion of the gas transfer line by spraying coolant from a nozzle facing the portion near the gas injection port, and by a gas flow means for creating a substantially dry gas flow through the nozzle to prevent the nozzle from becoming plugged with ice which is formed by freezing of moisture in the air when the coolant spray is ceased. Also, according to the present invention, the gas transfer line may be either a separation column, such as a capillary separation column used to separate a gas mixture having multiple components into each respective component thereof, or a simple conduit which operates without separation capability.

According to the present invention, the gas transfer line can be locally cooled to the temperature of the coolant by cooling a portion of the gas transfer line by spraying the coolant onto that portion. Thus, using the present invention, the sample introduced from the sample injection port can be condensed at the cooled portion of the gas transfer line. As a result, a single component is shown by a single peak when detecting each component of the sample with the detector.

The present invention provides an arrangement whereby a dry gas flows through the nozzle by the gas flow means, and therefore, the dry gas flows through the nozzle after the coolant spray in the cooling means has ceased. By the provision of flowing such a dry gas, moisturized air is prevented from entering inside the nozzle through its open end. Because the gas that flows through the nozzle owing to the gas flow means is a substantially dry gas which does not contain moisture, formation of ice caused by freezing of water existing in air, and thus plugging of the nozzle, can be prevented.

The sample concentration device of the present invention can condense the injected sample at the portion of the gas transfer line which is cooled by the coolant spray. However, if the humidity of the environment where the sample concentration device is employed is extremely high, a single component within the sample might be detected by plural split peaks.

This is considered to be due <6> to an ice formation at the cooled portion following the condensation of the water in highly humid air. As a result, a non-uniform thermal desorption takes place following a non-uniform melting of ice when external heating is later applied. The portion of the gas transfer line that is cooled is the lowest temperature portion thereof, and the gas transfer line has a temperature gradient such that the temperature increases with the distance away from this portion. When such a temperature gradient is formed, broad portions with temperatures near the freezing point of water are generated at both ends of the cooled portion and the formation of ice takes place at these ends. This ice melts and evaporates as a result of heat of the air in the constant temperature chamber when the coolant jet is stopped. The temperature of the gas transfer line is, therefore, considered to become non-uniform based on the place or situation of the ice formation.

The present inventors continued investigations utilizing the aforementioned findings and have discovered a means by which the formation of ice can be largely prevented by installing one or more jackets made of a material having a higher thermal conductivity than that of the gas transfer line disposed at least on both sides of the portion to be cooled by the coolant spray.

In the sample concentration device of the present invention, a gas transfer line is provided which is equipped with one or more outer jackets at the portion to be cooled by the cooling means, wherein such outer jacket(s) is/are made of a material having a thermal conductivity higher than that of the gas transfer line.

In the gas sample condensation device having a gas transfer line equipped with one or more outer jackets, the material for constructing the outer jacket has a thermal conductivity higher than that of the gas transfer line and can be, therefore, readily cooled to the temperature of the coolant temperature. As a result, the portion of the gas transfer line where the outer jacket is installed is cooled via this outer jacket.

On the other hand, the rest of the gas transfer line which does not have the outer jacket disposed thereon is not cooled to the same degree as the portion having the outer jacket thereon due to its lower thermal conductivity, and its temperature is kept about the same as that of the air in the constant temperature chamber. Because of this fact, a steep temperature gradient occurs at both ends of the outer jacket, and the areas of the gas transfer line that are cooled down to a temperature below the freezing point of water are kept minimal. The formation of ice can, therefore, be largely prevented.

Because the places where formation of ice takes place are at both ends of the cooled portion, as mentioned previously, the outer jackets should be installed at least at both ends of the cooled portion. In such a case, there is an exposed portion of the gas transfer line at a position between the installed outer jackets. However, sufficient cooling of the gas transfer line is still achieved at the exposed portion even without the outer jacket since this is the portion that is cooled most by direct contact with the coolant spray.

The outer jacket is constructed from materials having a higher thermal conductivity than those used for the gas transfer line, which is constructed for example from materials such as stainless steel or fused silica. Examples of these materials are graphite, or one of metals chosen from the following list of gold, silver, copper, iron, platinum, aluminum, tungsten, brass, platinum palladium, and platinum rhodium. The most preferred materials for construction from among the above list of metals are gold, silver or copper. Although gold and silver are expensive, they have excellent durability in a high temperature environment.

In a preferred embodiment of the invention, instead of an outer jacket, a tube having a diameter a few millimeters greater than that of the outer jacket and connected in a T-shape to the tip of the nozzle can be installed, so that the coolant can be sprayed on the gas transfer line which is inserted in this tube.

According to the aforementioned configuration, upon spraying of the coolant from the nozzle onto the gas transfer line, the region inside of the nozzle and the tube becomes completely filled with the coolant and the gas generated by its vaporization. Accordingly, highly moist air in the constant temperature chamber is prevented from entering into the tube. Ice formation around the portion of the gas transfer line which is inserted in the tube is, therefore, definitely prevented when spraying of the coolant is ceased.

Also, after the coolant spray is stopped, it becomes necessary to thermally desorb the sample that was condensed in the gas transfer line by rapidly heating the cooled portion with hot air in the constant temperature chamber. The cooled portion of the gas transfer line, would be difficult to heat rapidly if the diameter of the tube is small, because hot air cannot readily enter into the tube.

In order to rapidly heat the inside of the tube after stoppage of the coolant spray, both ends of the tube are preferably formed to have a trumpet-like shape, that is, having a diameter which increases towards the ends of the tube. With this trumpet-like design, hot air in the constant temperature chamber can readily penetrate into the tube, and the inside of the tube can be rapidly heated after the coolant spray has been stopped.

Such a trumpet-like design of tube the may result in allowing highly humid air to enter into the tube during spraying of the coolant, wherein ice formation around the gas transfer line may result. Such air penetration can, however, be avoided by using a sufficiently high flow rate for the coolant spray.

In preferred embodiment, the nozzle is further equipped with a heating means which serves to heat the temperature of the environment surrounding the portion of the tube that is cooled by the coolant spray. In particular, the environment is heated by a hot gas having a temperature higher than that of the coolant, by flowing the hot gas into the cooled portion, to replace the cooled environment, immediately after the coolant spray is stopped. Examples of such a hot gas, having a temperature higher than that of the coolant, are nitrogen or carbon dioxide either heated or kept at an ambient temperature.

In the sample concentration device of the present invention, the cooling means includes an fixed gas supply source, a first conduit connecting the fixed gas supply source with the nozzle, a liquefying means for cooling and liquefying the fixed gas flowing through the first conduit by immersing a part of the conduit in a coolant, and an open-close valve to open and close the first conduit. The gas flow means includes a second conduit that branches away from the first conduit between the fixed gas supply source and the liquefying means, and which joins the first conduit at a position downstream from the liquefying means. The open-close valve is installed at a position between the branching point where the first conduit branches off of the second conduit and the joining point where the first conduit joins the second conduit.

According to the aforementioned configuration, inert gas is supplied from the fixed gas supply source to the first conduit by opening the open-close valve when the coolant is intended to be sprayed out of the nozzle. The fixed gas is liquefied by the liquefying means while flowing through the first conduit and is supplied to the nozzle.

At this time, while inert gas is being supplied from the fixed gas supply source to the second conduit that branches from the first conduit at a position upstream of the open-close valve, the fixed gas flows into the first conduit again at a place downstream from the liquefying means. By this arrangement, the coolant in the first conduit is pressurized by the fixed gas supplied from the second conduit and is sprayed out of the nozzle.

Closing of the open-close valve cuts off supply of the inert gas to the first conduit and halts the coolant spray. On the other hand, fixed gas continues to be supplied to the second conduit constituting the gas flow means. As a result, only fixed gas flows out of the nozzle, and penetration of air containing moisture into the inside of the nozzle through its open end is prevented.

In this configuration, the supplied fixed gas can be shared by the cooling means and the gas flow means, and the construction of the device can be simplified. The device having the above-described configuration can have the back end of the nozzle either open-ended or close-ended. Also, the first conduit can either be placed adjacent the open back-end of the nozzle or attached air-tightly to the closed back-end of the nozzle.

If the back end of the nozzle is open, air is sucked into the nozzle when inert gas is sprayed out of the nozzle. Water in the air, then, condenses and causes ice formation around the cooled portion of the gas transfer line when moisture in the environment is extremely high.

In the device having the aforementioned configuration, the back-end of the nozzle is, therefore, preferably kept closed. This can prevent ice formation due to air being sucked in from the back-end of the nozzle when the liquefied inert gas is sprayed out of the nozzle.

The sample concentration device of the present invention can use liquid nitrogen or liquefied carbon dioxide as the coolant. The device can also be used together with analytical instruments such as a gas chromatograph.

BRIEF DESCRIPTION OF THE DRAWINGS

FIG. 5(a) is a diagonal view showing a design for the back-end of the nozzle shown in FIG. 4.

FIG. 5(b) is a descriptive cross-section view showing a design for the back-end of the nozzle shown in FIG. 4.

FIG. 6 is a descriptive cross-sectional view of another design for the back-end of the nozzle shown in FIG. 4.

DETAILED DESCRIPTION OF THE PREFERRED EMBODIMENTS

Figure 1:
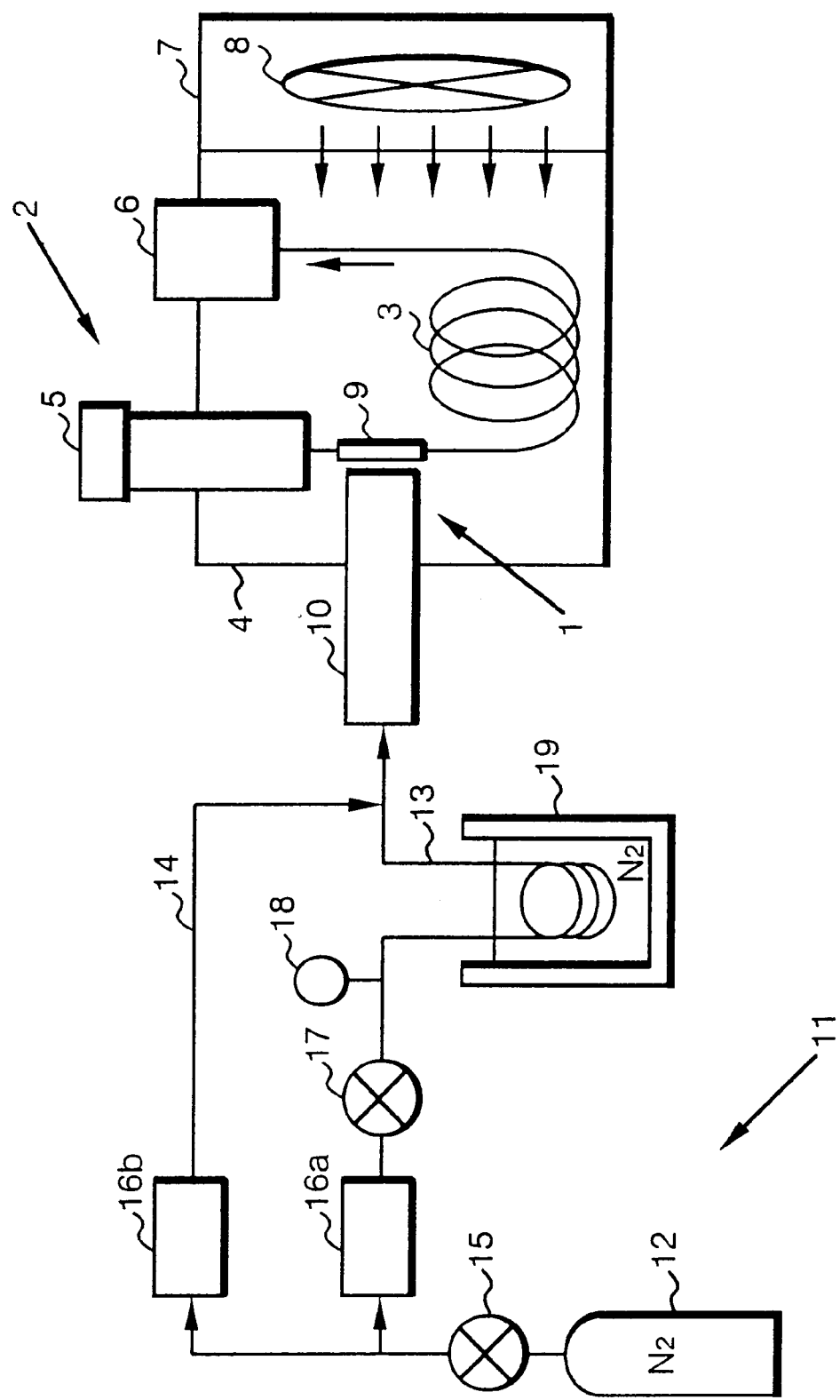
FIG. 1 is a depiction of the system configuration illustrating an example of the sample concentration device of the present invention.

In the first embodiment of the present invention, the sample concentration device 1 is to be installed in a gas chromatograph 2 as shown in FIG. 1. The gas chromatograph 2 is equipped with a constant temperature chamber 4 that houses a separation column 3. At one end of the separation column 3, a sample injection port 5 is installed and a detector 6 is located at the other end thereof. The constant temperature chamber 4 is heated on the inside thereof to a desired temperature using a heater 7 and fan 8. A mass spectrometer or flame ionization detector is an example of a device which can be used as the detector 6.

The sample concentration device 1 is equipped with an outer jacket 9, in which the separation column 3 is inserted. The outer jacket 9 is located at a position close to he sample injection port 5. This outer jacket 9 comprises a material having a thermal conductivity higher than that of the separation column 3. An example of such a material is graphite or one of the metals selected from the following list: gold, silver, copper, iron, platinum, aluminum, tungsten, brass, platinum palladium, and platinum rhodium.

The sample concentration device 1 is further equipped with a nozzle 10 installed to face the outer jacket 9, and a liquid nitrogen supply system 11 that supplies liquid nitrogen to the nozzle 10. The liquid nitrogen supply system 11 is composed of nitrogen gas cylinder 12, a nitrogen-liquefying conduit 13, and a nitrogen gas conduit 14. One end of the nitrogen-liquefying conduit 13 is connected to the nitrogen gas cylinder 12 via a main open-close valve 15, and the other end thereof is connected to the nozzle 10. Within the nitrogen-liquefying conduit 13, a flow controller 16a, an open-close valve 17, and a pressure gauge 18 to indicate the inner pressure of the conduit are arranged.

A portion of the nitrogen-liquefying conduit 13, between the nozzle 10 and the pressure gauge 18, is submerged in liquid nitrogen placed in a Dewar vessel 19. Because of this, nitrogen gas flowing in the nitrogen-liquefying conduit 13 is liquefied and liquid nitrogen is supplied to the nozzle 10. The nitrogen-liquefying conduit 13 is typically a stainless steel tube coated with a thermal insulating material or a fluorocarbon polymer tube.

The nitrogen gas conduit 14 branches from the nitrogen-liquefying conduit 13 downstream from the main open-close valve 15, and again joins the nitrogen-liquefying conduit 13 at a position downstream from the Dewar vessel 19. The nitrogen gas conduit 14 is further equipped with a flow controller 16b.

FIG. 2(a) shows the nozzle 10 comprising a cylindrical guide 20 made of stainless steel and a thin tube 21 made of stainless steel mounted therein. The cylindrical guide 20 penetrates through one of the walls 204 <15> of the constant temperature chamber 4. The back-end of the cylindrical guide 20 is tightly closed with a cover 22a, and the thin tube 21 is connected to the nitrogen liquefying conduit 13 by means of a connector 22b mounted on the cover 22a. The surface temperature of the thin tube 21 is determined by a thermocouple 23. The cover 22a is provided with windows 24 mounted on it, so that the end of the thin tube 21 can be seen within the cylindrical guide 21. The end 25 of the cylindrical guide 20 which is located within the constant temperature chamber 4 is welded to the outer jacket 9. The welding of end 25 to outer jacket 9 is deliberately made incomplete, so that there are gaps for the cooling fluids to escape around the outside of outer jacket 9.

The sample concentration device 1 according to this embodiment is operated as explained below.

When an analysis is carried out using the gas chromatograph 2, initially a carrier gas is introduced from a carrier gas source (not shown) to the separation column 3 via the sample injection port 5. Simultaneously, the interior of the constant temperature chamber 4 is heated to a desired temperature, for example 40° C., using the heater 7 and fan 8.

In the next step, liquid nitrogen is sprayed from the nozzle 10 to the outer jacket 9 by opening the main open-close valve 15 and the open-close valve 17 mounted on the nitrogen-liquefying conduit 13.

Opening of these valves results in nitrogen gas being supplied to the nitrogen-liquefying conduit 13 from the previously specified nitrogen gas cylinder 12. The flow rate of the nitrogen gas is controlled so as to be in a range of about 2–8 liters/min. by means of the flow controller 16a. The nitrogen gas is liquefied by being cooled under pressure while passing through the portion of the nitrogen-liquefying conduit 13 that is submerged in liquid nitrogen in the Dewar vessel 19.

Simultaneously, nitrogen gas is also supplied to the nitrogen gas conduit 14 from the nitrogen gas cylinder 12. The flow rate of the nitrogen gas is controlled so as to be in a range of about 10–40 ml/min. by the flow controller 16b, and the gas flows into the nitrogen-liquefying conduit 13 downstream from the Dewar vessel 19. Consequently, nitrogen gas supplied through the nitrogen gas conduit 14 and liquefied nitrogen in the nitrogen-liquefying conduit 13 are mixed, and the mixture is sprayed from the nozzle 10 onto the portion of the separation column 3 inserted in the outer jacket 9. Because the outer jacket 9 is made of a material having a higher thermal conductivity than the separation column 3, the portion of the separation column 3 inserted in the outer jacket 9 is cooled to the temperature of liquid nitrogen, or –196° C. On the other hand, the remainder of the separation column 13 is kept at the temperature of the constant temperature chamber 4, for example 40° C., thereby producing a steep temperature gradient at places near the ends of the outer jacket 9.

A sample consisting of multiple components is then injected into the sample injection port 5 using a microsyringe or the like. When the sample reaches the portion of the separation column 3 which is inserted in the outer jacket 9, all the components of the sample are condensed at once and concentrated at the portion which has been cooled to the low temperature.

Then, by closing the open-close valve 17, spraying of liquid nitrogen is stopped, and the temperature of the constant temperature chamber 2 is raised, at a desired rate, to a desired temperature, for example 15° C./min. and 160° C., using the heater 7 and fan 8. All of the components in the concentrated sample, then, desorb very quickly and each component is separated and detected by a single peak.

Upon closing the open-close valve in the aforementioned manner, spraying of the liquid nitrogen is ceased, but the supply of nitrogen gas from the nitrogen gas cylinder 12 to the nitrogen gas conduit 14 is maintained thereafter. As the nitrogen gas flows through the nitrogen gas conduit 14 to the nozzle 10, it continues to flow out of the open end of the nozzle 10 even after spraying of liquid nitrogen has been stopped.

As a consequence, penetration of moist air is prevented from entering into the nozzle 10 through the open end thereof. Because the nitrogen gas itself is substantially dry and does not contain any moisture, plugging of the nozzle 10 by formation of ice is prevented.

An example of an analysis of a gaseous sample, which was conducted using the device shown in FIG. 1 shall be described below.

The parts employed in the following example of the analysis were a stainless steel capillary column having an inner diameter of 0.25 mm and a length of 30 m, and with a 0.25 µm thick polyb (dimethylsiloxane) coating (Ultra Alloy-1 by Frontier Laboratories Limited), which serves as the separation column, and a flame ionization detector serving as the detecting device.

The outer jacket 9 was made of silver, and was mounted on the separation column 3. The nozzle 10, facing the outer jacket 9, comprised a stainless steel cylindrical guide 20 having a 2.1 mm inner diameter, a ⅛ inch outer diameter, and a length of 9 cm; and a thin stainless steel tube 21 having a 0.8 mm inner diameter and a 1.15 mm outer diameter. The nitrogen-liquefying conduit was comprised of a fluorocarbon polymer conduit having a 0.96 mm inner diameter and a 1.56 mm outer diameter.

In the present example, the inside temperature of the constant temperature chamber was heated to 40° C. by operating the heater 7 and fan 8, while the carrier gas (helium) was made to flow into the capillary separation column 3 at a rate of 1.2 ml/min. The sample concentration device 1 was then turned on to spray liquid nitrogen from the nozzle 10 onto the outer jacket 9 at a rate of 5 liters/min (based on volume at ambient temperature) and thereby cool the capillary column 3 via the outer jacket 9.

A standard sample solution comprising saturated hydrocarbons ranging in carbon numbers of from 5 to 10 (i.e., pentane, hexane, heptane, octane, nonane and decane) was placed in a sealed container and 3 µl of gas from a headspace thereof was injected into the sample injection port 5. A ¹⁄₅₀ portion of the gas was introduced into the capillary separation column 3 as the sample, and was condensed at the portion of the column 3 where the outer jacket was placed.

The liquid nitrogen spray was then stopped, and the temperature inside the constant temperature chamber 2 was raised from 40° C. to 160° C. at a rate of 15° C. per minute. The components of the gaseous sample were then separated from each other by the capillary separation column 3 and were detected by the flame ionization detector 6. Peaks corresponding to the components having carbon numbers from 6 to 9, thus obtained, are illustrated in the lower half of FIG. 3.

For comparison, components of a gaseous sample were analyzed using the flame ionization detector 6 using the same conditions as those in the preceding example, except for the absence of the outer jacket 9. Peaks corresponding to the components with carbon numbers thus obtained are shown in the upper half of FIG. 3.

Figure 3:
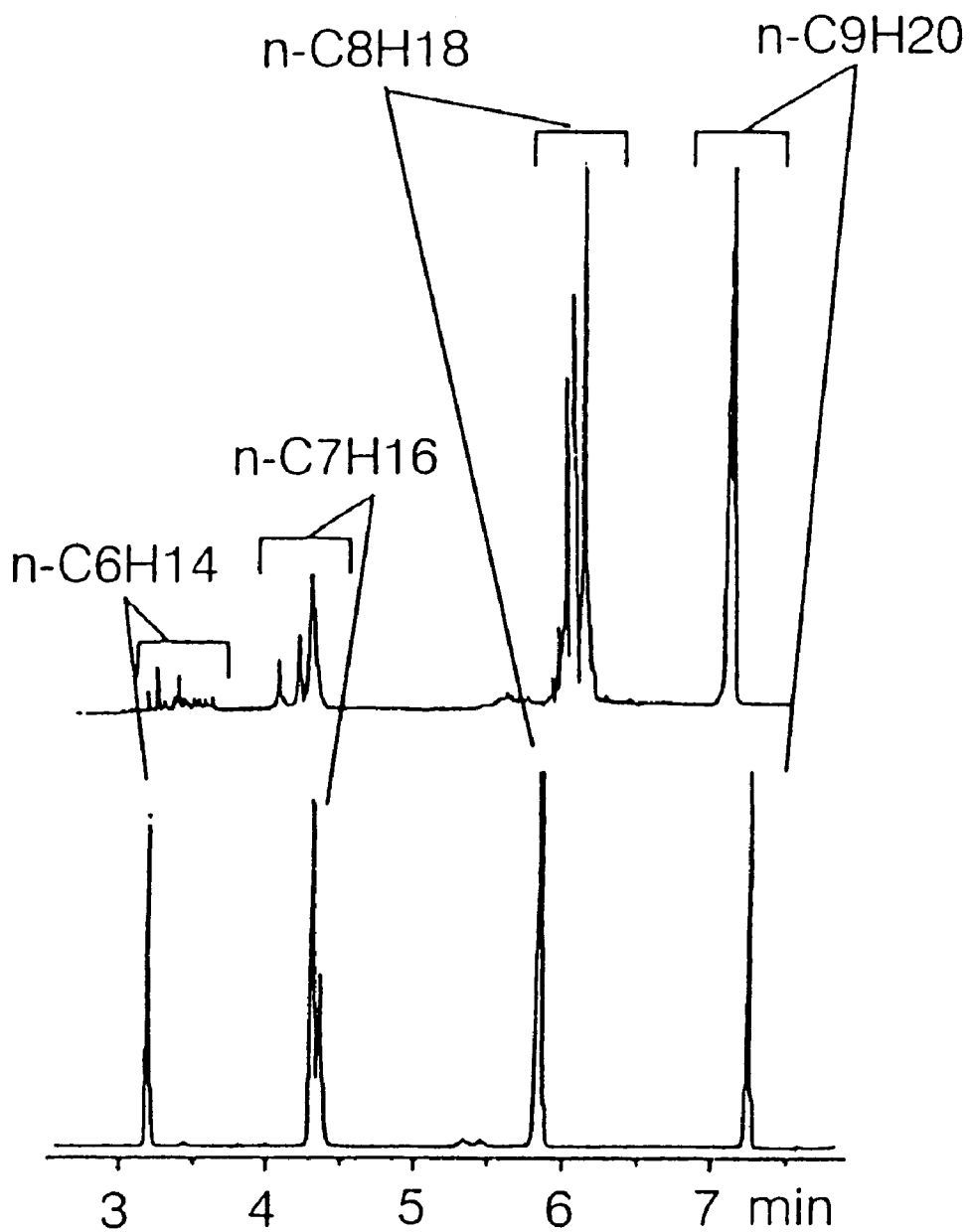
FIG. 3 is a chromatogram showing an analysis result produced by a gas analyzing apparatus using the sample concentration device shown in FIG. 1.

As apparent from FIG. 3, as shown in the example, each component having carbon numbers of from 6 to 9 (i.e., hexane, heptane, octane and nonane) can be detected by a corresponding single peak. On the other hand, these same components are detected by multiple peaks if the outer jacket 9 is absent.

Heptane was detected by a doublet peak in the example, as shown in the lower half of FIG. 3. This is due to the detection of isomers of heptane.

In the present embodiment, the outer jacket 9 is installed to cover the entire portion of the capillary column 3 where liquid nitrogen is sprayed from the nozzle 10. However, as shown in FIG. 2(c), the outer jacket 9 can also be installed, instead, at both ends of the portion where liquid nitrogen is sprayed. In this case, a zone of a few millimeters at the center of the portion where liquid nitrogen is sprayed is not covered by the outer jacket 9. Thus, this zone of the capillary column 3 is directly cooled by the liquid nitrogen spray.

Figure 4:
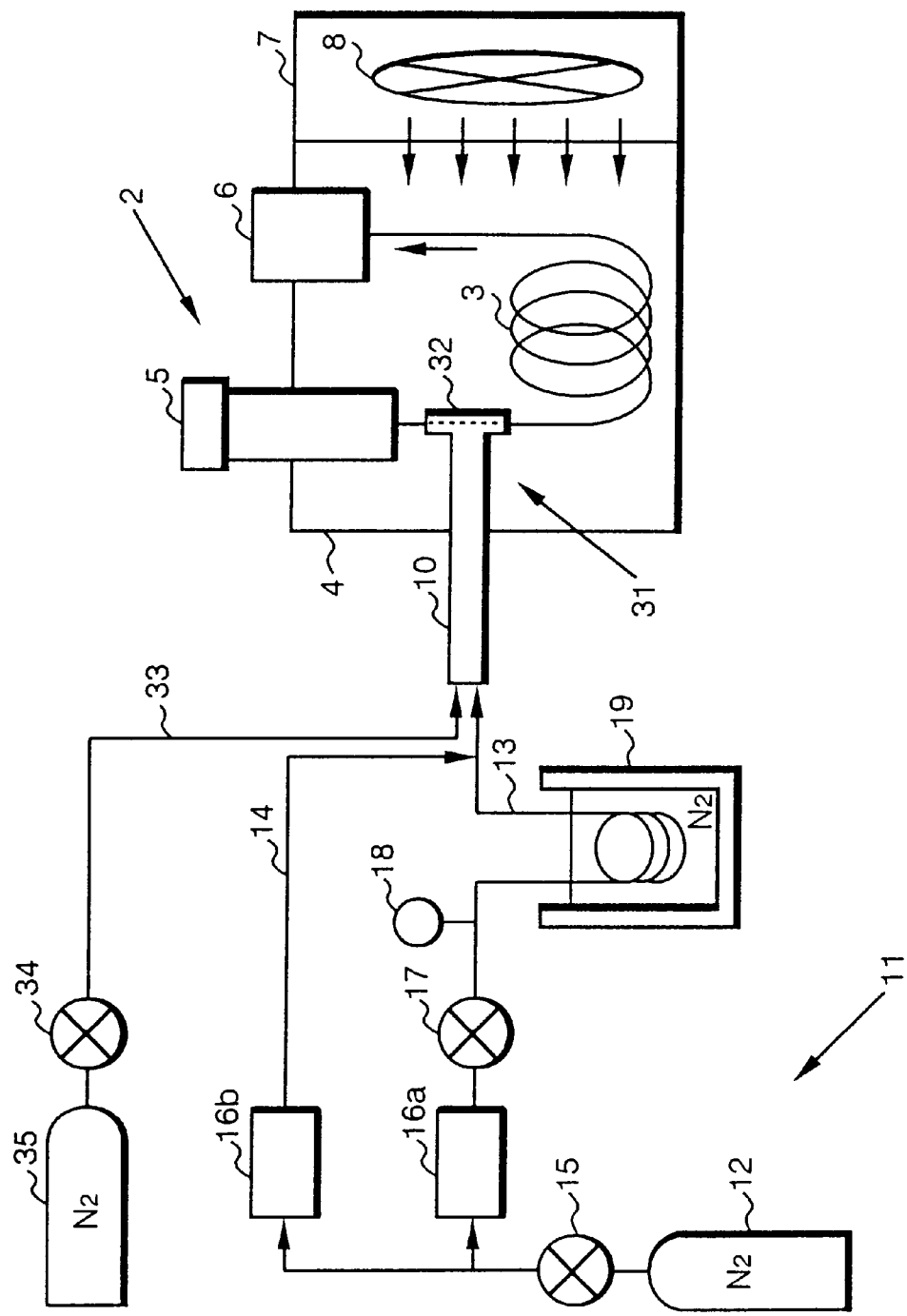
FIG. 4 is a depiction of the system configuration illustrating another example of the sample concentration device of the present invention.

Referring to FIG. 4, a concentration device 31 according to a second embodiment of the present invention shall be described.

The sample concentration device 31 has an identical configuration to that of the sample concentration device 1 shown in FIG. 1, except for arranging a cylinder 32 in place of the outer jacket 9, in addition to providing a heating gas conduit 33. The front-end of the nozzle 10 is fixed to the middle part of the cylinder 32 in a T-shape so that the nozzle and the cylinder 32 are constructed in one piece. The capillary column 3 is loosely inserted in the cylinder 32.

The heating gas conduit 33 is mounted on the back-end of the nozzle, and nitrogen gas is flowed through the nozzle 10 to displace the gas around the cooled portion and thereby heat the cooled portion of the capillary column. The heating gas conduit 33 is connected to a nitrogen gas cylinder 35 via an open-close valve 34. The gas supplied by the heating gas conduit 33 can also be air if desired. In this case, the heating gas conduit 33 is connected to a compressed air cylinder via the open-close valve 34.

In the sample concentration device 31, the back-end of the nozzle 10 can be either open, as shown in FIG. 5(a), or closed as shown in FIG. 6. When the back-end 36a of the nozzle 10 (cylindrical guide 20) is open, as in FIG. 5(a), the nitrogen liquefying conduit 13 is connected to the thin tube 21 by means of a mounting plate 37 arranged at the back-end 36a. The heating gas conduit 33, which penetrates through and is fixed to the mounting plate 37, is then inserted into the cylindrical guide 20.

When the back-end 36a is open, highly humid air tends to be pulled into the nozzle 10 upon spraying liquefied nitrogen therefrom as shown in FIG. 5(b). When this takes place, water present in the air may condense and freeze to form ice around the portion of capillary column 3 in the cylinder 32. This kind of phenomenon is frequently observed especially in environments having very high humidity, such as during the rainy season in Japan.

It is therefore preferred that the back-end 36a of the nozzle 10 (cylindrical guide 20) be closed, as shown in FIG. 6, so that humid air is prevented from being pulled in and ice formation does not occur.

According to the configuration shown in FIG. 6, the nitrogen-liquefying conduit 13 penetrates in an airtight manner through the closed back-end 36b, and is connected to the thin tube 21 via the back-end 36b. The heating gas conduit 33 also penetrates air-tightly through the closed back-end 36b and is inserted into the cylindrical guide 20.

Figure 2:
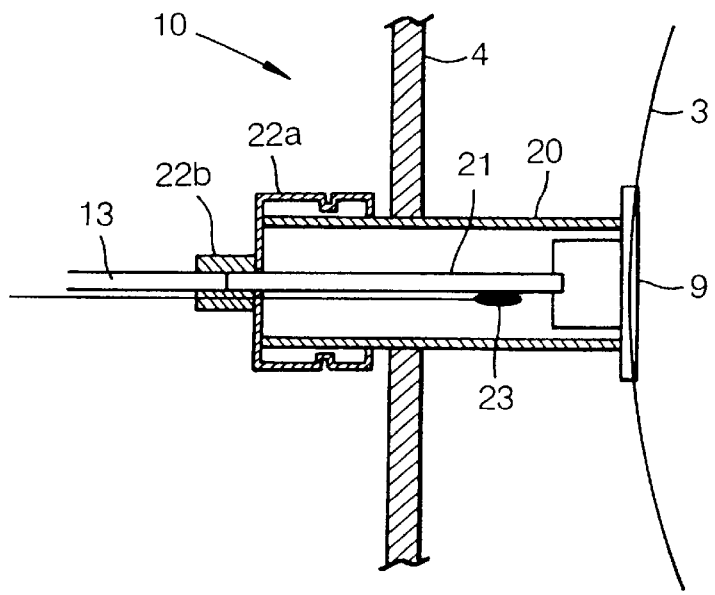
FIG. 2(a) shows an enlarged cross-sectional view of an essential part of the device shown in FIG. 1.
FIG. 2(b) is a diagonal view of an alternative example of the device shown in FIG. 1.
FIG. 2(c) is a cross-sectional view of an alternative example of the device shown in FIG. 1.
Figure 2:
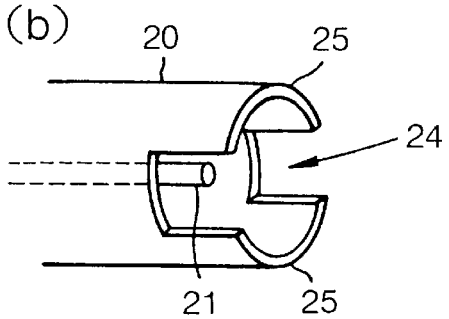
Figure 2C:
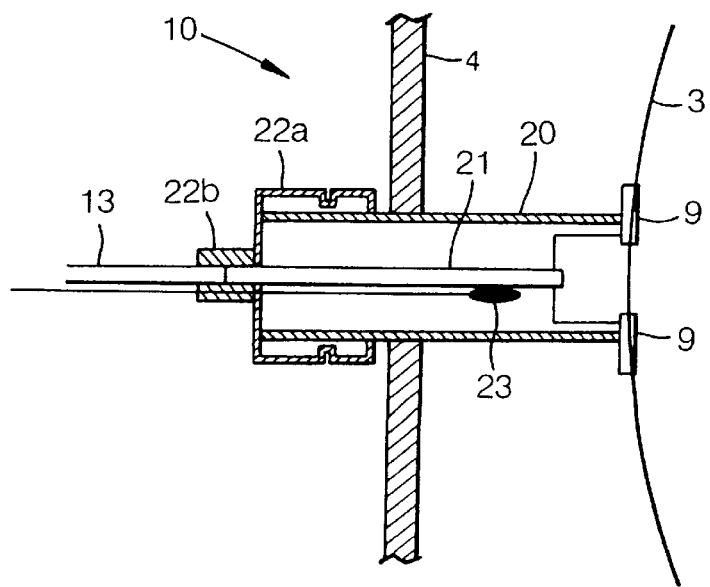

Although not shown in FIG. 5 and FIG. 6, the nitrogen-liquefying conduit is connected to the thin tube 21 by means of the same connector 22b shown in FIG. 2.

The sample concentration device 31 is operated in the following manner.

When the sample concentration device 31 is placed in operation, liquid nitrogen is sprayed from nozzle 10 onto the portion of the capillary column 3 located at the middle of the cylinder 32, for cooling the portion following the same procedure as that for the sample concentration device 1 shown in FIG. 1. The interior of the cylinder 32 is then filled with liquid nitrogen along with nitrogen gas generated by the evaporation of liquid nitrogen. Consequently, humid air inside the constant temperature chamber 4 is prevented from entering into the cylinder 32.

Then, following the same procedure for the sample concentration device 1 shown in FIG. 1, a sample is introduced into the capillary column, and thereafter is condensed at the cooled portion, whereupon the liquid nitrogen spray is stopped. At this time, in the sample concentration device 31, nitrogen gas is allowed to flow from the nitrogen gas cylinder to the nozzle 10 through the heating gas conduit 33 by opening the open-close valve 34 placed in the heating gas conduit 33 for a preset period. The atmosphere around the cooled portion inside the cylinder 31 is displaced by the nitrogen gas supplied from the heating gas conduit 33, and the cooled portion of the capillary column 3 is heated to the temperature of the nitrogen gas. After the cooled portion of the capillary column 3 has become heated, the open-close valve 34 is closed and the supply of nitrogen gas from the heated gas conduit is stopped.

By subsequently raising the temperature inside the constant temperature chamber 4 to a preset level, the condensed sample desorbs thermally. During this time, the cooled portion of the interior of the cylinder 32 is heated to the temperature of the nitrogen gas supplied from the heating gas conduit 33, as described above. The air inside the constant temperature chamber 4 that is at a preset temperature then flows into the cylinder from both ends thereof, whereby the cooled capillary column 3 is rapidly heated.

Nitrogen gas is also arranged to always flow into the cylinder 32 by means of the nitrogen gas conduit 14. Such a nitrogen gas flow does not interfere with the entry of air, because the flow rate of the nitrogen gas is set at only about 10–40 ml/min. as previously described.

The aforementioned sample is then desorbed instantly, and each component is separated by the capillary column and detected.

Figure 7:
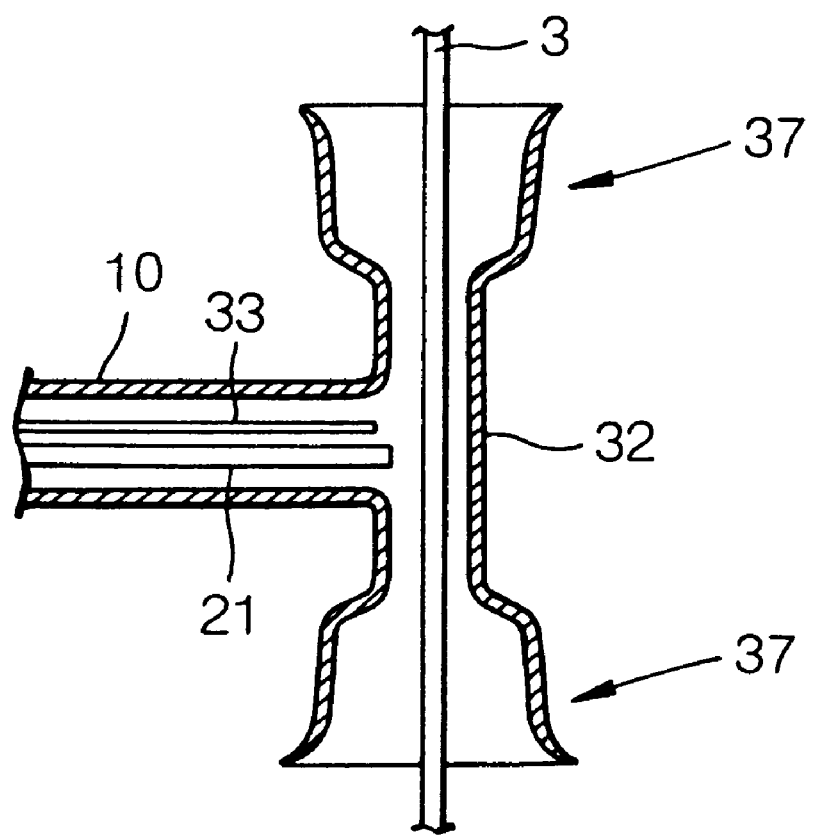
FIG. 7 is a descriptive cross-sectional view of an alternative design for the tube shown in FIG. 2.

In order to facilitate the process whereby heated air in the constant temperature chamber 4 flows into the cylinder 32, it is preferred that both ends of the cylinder 32 be made with a trumpet-like design 37, as illustrated in FIG. 7.

In the sample concentration device 31, nitrogen gas is arranged to flow in the heating gas conduit 33 when the liquid nitrogen spray is stopped. The gas flow in the heating gas conduit, however, can also be compressed air, as mentioned previously, or any gas having a temperature higher than that of liquid nitrogen, for example carbon dioxide.

The devices used in the examples, according to the present embodiments, are equipped with a main open-close vale 15 and a further open-close valve 17. The open-close valve can be omitted if a three-way valve is used in place of the open-close valve 15. In that case, when liquid nitrogen is sprayed, both the nitrogen-liquefying conduit 13 and the nitrogen gas conduit 14 are connected to the nitrogen gas cylinder by means of the three-way valve. When the liquid nitrogen spray is stopped, only the nitrogen gas conduit 14 remains connected to the nitrogen gas cylinder 12 by means of the three-way valve.

The nitrogen gas conduit 14 can also be separated from the nitrogen-liquefying conduit 13, in which case the latter is connected to a liquid nitrogen containing Dewar vessel instead of to the nitrogen gas cylinder 12.

The gas which flows to prevent plugging of the nozzle 10 need not be limited to nitrogen gas, and any gas that is substantially dry can be employed.

Although according to the described examples of the present embodiments, liquid nitrogen was sprayed from the nozzle 10 for cooling the capillary column 3, liquid carbon dioxide may also be used in place of liquefied nitrogen.

In the examples of the present embodiments, cases of applying the sample concentration device of the present invention to a gas chromatograph 2 have been described. However, applications of the sample concentration device of the present invention are not limited solely to use with a gas chromatograph. For example, the device can also be applied to equipment which serves to guide a sample to a mass spectrometer or the like, for analysis using a conduit which does not have separation capability. Another example for use of the present invention is for a purge-and-trap device, which condenses within a conduit volatile substances, such as odor causing materials or fragrances generated by heating a few grams of solid samples, such as flowers, leaves or wood products.

What is claimed is:

1. A sample concentration device for concentrating a sample in a vicinity of a sample injection port, when said sample is analyzed by introducing said sample into a detection device through a gas transfer line which is housed in a constant temperature chamber, comprising:

cooling means for cooling a portion of said gas transfer line by spraying a coolant from a nozzle disposed facing said gas transfer line in the vicinity of said sample injection port; and gas flow means for creating a substantially dry gas flow through the nozzle to prevent said nozzle from becoming plugged with ice which is formed by freezing of moisture in the air when the coolant spray is ceased.

2. The sample concentration device according to claim 1, wherein said gas transfer line is equipped with an outer jacket disposed at least on respective both ends of the portion cooled by said cooling means, and wherein said outer jacket is formed of a material having a thermal conductivity higher than said gas transfer line.

3. The sample concentration device according to claim 2, wherein said outer jacket is disposed on said gas transfer line so as to surround the entirety of the portion cooled by said cooling means.

4. The sample concentration device according to claim 2, wherein said outer jacket is formed of graphite or a metal material selected from from the group consisting of gold, silver, copper, iron, platinum, aluminum, tungsten, brass, platinum palladium and platinum-rhodium.

5. The sample concentration device according to claim 1, wherein said nozzle comprises a cylindrical member connected at an end thereof in a T-shaped formation, wherein said coolant is sprayed onto said gas transfer line which is inserted into said cylindrical member.

6. The sample concentration device according to claim 5, further comprising increasing diameter portions which expand outwardly on both ends of the cylindrical member.

7. The sample concentration device according to claim 5, wherein said nozzle further comprises heating means for flowing a gas having a temperature greater than said coolant to said cylindrical member, when spraying of said coolant is halted, and displacing the environment of the portion cooled by said coolant inside said cylindrical member by said gas, for heating by the gas temperature.

8. The sample concentration device according to claim 5, wherein the gas which is flowed to the cylindrical member by said heating means is a fixed gas.

9. The sample concentration device according to claim 1, wherein:

said cooling means comprises a fixed gas supply source, a first conduit interconnecting said fixed gas supply source and said nozzle, liquefying means having means for immersing a portion of said first conduit in a coolant for cooling and liquefying the fixed gas which flows though said first conduit, and an open-close valve for opening and closing said first conduit;

said gas flow means comprises a second conduit branching from said first conduit at a position between said fixed gas supply source and said liquefying means, and which joins with said first conduit downstream from said liquefying means; and said open-close valve is disposed between a branch point at which said first conduit branches from said second conduit and a joining point at which said first conduit joins with said second conduit.

10. The sample concentration device according to claim 9, wherein said first conduit is connected to an open-ended end portion of said nozzle.

11. The sample concentration device according to claim 9, wherein said first conduit is connected air-tightly to an end portion of said nozzle.

* * * * *